United States Patent [19]

Smith et al.

[11] Patent Number: 5,672,803
[45] Date of Patent: Sep. 30, 1997

[54] METHOD FOR MAKING TRANS NON-CONJUGATED DIOLEFINS

[75] Inventors: Robert Scott Smith; Jos Peter Wristers, both of Houston, Tex.

[73] Assignee: Exxon Chemical Patents Inc., Wilmington, Del.

[21] Appl. No.: 562,675

[22] Filed: Nov. 27, 1995

Related U.S. Application Data

[63] Continuation of Ser. No. 176,166, Dec. 30, 1993, abandoned.

[51] Int. Cl.$^6$ ............................ C07C 6/00; C07C 6/02
[52] U.S. Cl. ...................... 585/646; 585/601; 585/643; 585/647
[58] Field of Search ...................... 585/601, 643, 585/646, 647

[56] References Cited

U.S. PATENT DOCUMENTS

| | | |
|---|---|---|
| 3,405,194 | 10/1968 | Iwamoto et al. . |
| 3,424,811 | 1/1969 | Mango . |
| 3,502,738 | 3/1970 | Cramer . |
| 3,539,652 | 11/1970 | Schneider . |
| 3,565,967 | 2/1971 | Collette et al. . |
| 3,641,174 | 2/1972 | Lyons . |
| 3,641,189 | 2/1972 | Turner et al. . |
| 3,676,520 | 7/1972 | Heckelsberg . |
| 3,792,101 | 2/1974 | Hattori et al. . |
| 3,927,137 | 12/1975 | Bryson . |
| 4,010,216 | 3/1977 | Yoo . |
| 4,795,734 | 1/1989 | Chauvin et al. . |
| 5,025,111 | 6/1991 | Hazel . |
| 5,113,033 | 5/1992 | Myers et al. ............... 585/506 |

FOREIGN PATENT DOCUMENTS

| | | |
|---|---|---|
| 1 103 976 | 2/1968 | United Kingdom . |
| 1 117 968 | 6/1968 | United Kingdom . |

OTHER PUBLICATIONS

Kawai, et al., *Journal of Molecular Catalysts*, 1987, 39, 369–382.

Warel, et al., *Synthesis*, 1987, 935–937.

*Primary Examiner*—Ponnathapura Achutamurthy
*Attorney, Agent, or Firm*—Linda K. Russell

[57] ABSTRACT

A method is provided for selectively producing a trans-geometrical isomer of non-conjugated diolefins. The method comprises treating a starting non-conjugated diolefin isomer or mixture of isomers, a first mono-olefin and a second mono-olefin with a metathesis catalyst under selected reaction conditions to produce a product with greater than 80% trans-geometrical isomer content. In a preferred embodiment, 1,4-hexadiene, ethene, and propene contact a $Re_2O_7$ catalyst and are converted to a reaction product mixture with above 80% trans-1,4-hexadiene.

20 Claims, No Drawings

METHOD FOR MAKING TRANS NON-CONJUGATED DIOLEFINS

This is a continuation of application Ser. No. 08/176,166, filed Dec. 30, 1993, now abandoned.

TECHNICAL FIELD OF THE INVENTION

The present invention relates to the chemistry of hydrocarbon compounds containing non-conjugated double bonds and, more particularly, to the selective production of trans non-conjugated diolefins such as trans-1,4-hexadiene.

BACKGROUND OF THE INVENTION

Non-conjugated diolefins are useful as monomers or co-monomers in polymer synthesis. Trans-1,4-hexadiene is a reactant of choice in certain processes, such as that described in U.S. Pat. No. 3,565,967 which prefers a trans isomer content greater than 80% in the manufacture of ethylene-propylene-diene monomer (EPDM) elastomers. Prior art methods for producing 1,4-hexadiene with trans isomer content greater than 80% include U.S. Pat. No. 3,565,967 (using a soluble nickel compound) or U.S. Pat. No. 3,502,738 (using a rhodium catalyst). However, these prior art methods use expensive catalysts and require corrosive reagents. In contrast, cis-1,4-hexadiene can be produced with good conversion and high selectivity by the methods of U.S. Pat. Nos. 3,539,652, or 3,405,194, using a relatively inexpensive cobalt catalyst system. The cobalt catalysts are less corrosive than either the nickel catalyst of U.S. Pat. No. 3,565,967 or the rhodium catalyst of U.S. Pat. No. 3,502,738.

Various authors refer to transition metal and Group VIII metal catalyzed olefin reactions of the type:

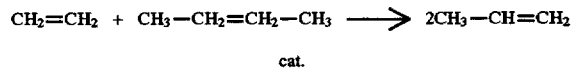

as metathesis or disproportionation. For clarity, the term metathesis as used here includes those reactions referred to as disproportionation, as well as those referred to as metathesis by other authors. The prior art contains numerous examples of metathesis reactions of simple olefins in the presence of various metal catalysts. In simple olefin metathesis, the cis/trans ratio of products is found to be near the thermodynamic equilibrium point or only slightly to favor the trans isomer.

Metathesis of acyclic 1,4-dienes has not been studied as extensively as simple olefins. However, Kawai, et al., *Journal of Molecular Catalysts*, 1987, 39, 369–382 describes the synthesis of 1,4-dienes over a $CsNO_3$-$Re_2O_7$-alumina catalyst, but the isomer content of recovered materials was not disclosed. U.S. Pat. No. 5,025,111 teaches metathesis of 1,4-hexadienes with ethene in the presence of $Re_2O_7$ promoted by tetra-alkyl tins or tri-alkyl aluminums as a method to prepare 1,4-pentadienes. U.S. Pat. No. 3,641,174 describes metathesis of 1,4-dienes with a soluble Group VIII transition metal complex under conditions where significant double bond position isomerization also occurred. However, the prior art has not heretofore provided a method for producing the trans non-conjugated diolefin geometrical isomer by metathesis using relatively inexpensive non-corrosive catalysts, or employing selected mixtures of three or more olefins and diolefins to produce mixtures of non-conjugated diolefins having a trans isomer content greater than 80%.

SUMMARY OF THE INVENTION

This invention relates to a method for making trans non-conjugated diolefins of structure which comprises:

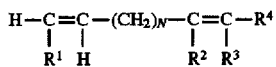

where N is a positive integer from 1 to 5 and $R^2$, $R^3$, and $R^4$ are each hydrogen or an alkyl or 1 to 5 carbons and $R^1$ is an alkyl of 1 to 5 carbons
which comprises:

a. selecting isomerizable non-conjugated diolefin with structure

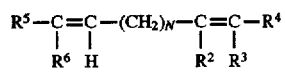

where N is a positive integer from 1 to 5 and $R^2$, $R^3$, $R^4$, and $R^5$, are each hydrogen or an alkyl or 1 to 5 carbons and $R^1$ and $R^6$ are each an alkyl or 1 to 5 carbons and $R^2$, $R^3$, and $R^4$ are the same as in the trans non-conjugated diolefin and when $R^5$ is hydrogen and $R^6$ is an alkyl, the adjacent double bond is greater than 50% cis;

b. selecting a first olefin from the group consisting of:
(1) olefins having the structure

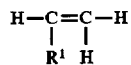

(2) olefins having the structure:

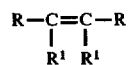

and
(3) mixtures of olefin 1 and olefin 2
where $R^1$ is the same as $R^1$ of the trans non-conjugated diolefin;

c. selecting a second olefin which is different than the first olefin from the group consisting of
(1) an olefin having the structure:

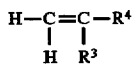

(2) an olefin having the structure:

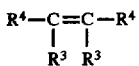

and
(3) mixtures of olfin 1 and olefin 2 where $R^3$ and $R^4$ are the same as $R^3$ and $R^4$ of the diolefin selected in step a;

d. mixing the selected diolefin with the selected first olefin and the selected second olefin in a mole ratio of first olefin to diolefin within the range of about 0.2/1 to 100/1 and a mole ratio of the selected second olefin to diolefin within the range of about 0.2/1 to 100/1 to form an olefin reaction mixture; and e. contacting the olefin reaction mixture in a reaction vessel at a temperature in the range $-30°$ to $200°$ C. at a pressure in the range of 140 to 2,000 psig (1,070 to 14,000 kPa) with a non-acidic metathesis catalyst selected from the group consisting of homogeneous metal catalysts and heterogeneous metal catalysts wherein the metal is selected from the group consisting of W, Mo, Co, Ta, Nb, Cr, and Re, to form the selected trans nonconjugated diolefin isomer product.

In a preferred embodiment, the invention provides a method of preparing trans-1,4-hexadiene consisting essentially of contacting an olefin reaction feed mixture comprising cis-1,4-hexadiene, ethene and an olefin selected from the group consisting of propene, 2-butene, and mixtures of propene and 2-butene, with a metathesis catalyst which comprises one or more compounds selected from the group consisting of rhenium oxide ($Re_2O_7$), tungsten oxide ($WO_3$), cobalt oxide (CoO), or molybdenum oxide (MoO3); the selected catalyst compound being loaded onto a solid support at a loading of between 5 and 30 wt % in a fixed catalyst bed.

Although any effective metathesis catalyst may be used, an advantage of the invention is that inexpensive and non-corrosive catalysts can be used. The currently preferred catalyst is $Re_2O_7$ supported on alumina. Optionally, the catalyst may be promoted by a tetraalkyl tin or a trialkyl aluminum compound. The tetraalkyl tin or trialkyl aluminum promoters will preferably have from 1 to 5 carbons in each alkyl group which may be the same or different, however, the specific identity of the alkyl groups is not critical. Tetramethyl tin is a preferred promoter. The invention provides an improved method for producing commercially important isomer mixtures of diolefins such as 1,4-hexadiene wherein the trans isomer content is greater than 80%, a preferred feed material in the manufacture of ethylene-propylene-diene monomer (EPDM) elastomers as described in U.S. Pat. No. 3,565,967.

DETAILED DESCRIPTION OF THE INVENTION

In general, conversion to trans isomers is carried out by mixing a non-conjugated diolefin feed with a first olefin selected such that one of the double bonds of the diolefin molecule will be regenerated after a metethesis reaction with the second olefin and a first olefin selected, so that metathesis between the diolefin and the first olefin at the second double bond can result in formation of a non-conjugated diolefin under conditions that lead to selective formation of the trans geometrical isomer.

In a model system illustrated in the examples below, the conversion of cis or mixed cis/trans 1,4-hexadienes to a reaction product having a trans content greater than 80%, is carried out by contacting an olefin reaction mixture of 1,4-hexadiene, ethene, and either propene or 2-butene with a non-acidic olefin metathesis catalyst. The product mixture is found to contain ethene, propene, trans and cis 2-butene, 1,4-pentadiene, trans and cis 1,4-hexadienes, and heavier olefins. In a preferred embodiment, the 1,4-hexadienes are separated from the reaction mixture. In an especially preferred embodiment, the other products and remaining starting materials are recycled to the metathesis reactor. The metathesis catalyst can be either homogenous or heterogeneous, provided, however, that the catalyst must not cause substantial double bond positional isomerization. In a preferred embodiment, the catalyst is in a fixed bed and the reaction is carried out as a continuous process.

The starting non-conjugated diolefins can be prepared by known methods such as metal catalyzed dimerization reactions between simple olefins and conjugated dienes, as are well known to those skilled in the art. For example, 1,4-hexadiene can be prepared by the reaction of ethene and butadiene in the presence of a suitable catalyst. U.S. Pat. No. 3,539,652 or U.S. Pat. No. 3,405,194 provide reaction conditions for making predominantly cis-1,4-hexadiene using a cobalt compound as a catalyst. In practicing the invention, the trans/cis ratio of the starting diolefin material is not critical. It is, of course, preferable to obtain the starting non-conjugated diolefin in good yield and with good reactant conversion, using inexpensive, non-corrosive metal compounds as catalysts to obtain the lowest-cost feed stock. Compounds of rhenium, cobalt, nickel, palladium, iron, and other Group VIII and transition metals can be used to prepare non-conjugated dienes from lower molecular weight starting materials. U.S. Pat. No. 4,010,216; U.S. Pat. No. 3,792,101; and U.S. Pat. No. 3,927,137 teach the preparation of non-conjugated diolefins suitable as starting materials for the present method. Suitable metathesis catalyst may be either heterogeneous such as a supported $Re_2O_7$, CoO/$MoO_3$ or $WO_3$ on alumina or silica or homogeneous such as $Mo(NO)_2Cl_2$ ($PPh_3)_2$/$ETAlCl_2$, $Mo(CO)_4$ (Pyridine)$_2$/$Bu_4NCl$/$Me_3Al_2Cl_3$ or various carbene complexes of Ta, Nb, or Cr, and V.

The metathesis reaction is carried out at a temperature in the range of −30° to 200° C., preferably between −10° and 100° C., and more preferably between 0° and 30° and at a pressure between 140 and 2000 psig (1,070 and 14,000 kPa), preferably between 400 and 1500 psig (2,900 and 10,400 kPa), and more preferably between 500 and 800 psig (3,500 and 5,500 kPa). The metathesis catalyst must not cause substantial positional isomerization. For this reason, the metathesis catalyst and its support must have essentially no acidic character. As used in this application, a catalyst is non-acidic if in use it does not cause substantial positional isomerization.

To produce a non-acidic catalyst, the metathesis catalyst can be treated so as to lower acid strength. For example, British patent 1,117,968 teaches treatment of CoO/$MoO_3$ on alumina with KOH to reduce acidity of the catalyst. The amount of catalyst used is selected to carry out to the isomerization at an acceptable rate. The catalyst amount will be affected by the surface area of catalyst available, the reactor configuration, and throughput conditions. The catalyst amount is not critical and may be adjusted and selected by techniques well known to those skilled in the art.

A particularly preferred group of heterogeneous catalysts are composed of $Re_2O_7$ on alumina which have been found to be especially effective. Metathesis reactions with $Re_2O_7$ on alumina occur at low temperatures where the acidity of the support is low. The acidity of $Re_2O_7$ on alumina can be further lowered by addition of alkali metal ions such as the techniques described in U.S. Pat. No. 3,424,811 or British patent 1,117,968. The $Re_2O_7$ on alumina catalysts can be prepared in a number of ways, including those described in U.S. Pat. No. 3,676,520 or U.S. Pat. No. 4,795,734 or British patent 1,103,976. The ratio of $Re_2O_7$ to support is not critical. The catalyst loading may be in the range of 5 to 30 weight percent, typically 10 to 20 weight percent, preferably, 10 to 14 percent. Optionally, $Re_2O_7$ catalyst performance may be improved by use of a promoter such as a tetraalkyl tin, according to Warel, et al., *Synthesis* 1987, 935–937. The $Re_2O_7$ catalyst is normally activated, for example, the air activation described in U.S. Pat. No. 3,641,189.

The reaction may be run continuously or in discrete batches. Inert diluents such as hexane, cyclopentane, propane, butane, cyclohexane, benzene or toluene may be used in the reaction mixture.

In a preferred embodiment, a feed comprising cis-1,4-hexadiene content greater than 50%, preferably greater than about 90%, is mixed with ethene and propene to form an olefin reaction feed mixture (or feed). The mole ratio of ethene to 1,4-hexadiene may be from 0.2/1 to 100/1, but is preferably in the range of 1/1 to 10/1 and, more preferably, 2/1 to 4/1. It is desirable to use sufficient ethene to limit formation of heavier metathesis products, but not so much that the composition of 1,4-hexadiene in the product becomes economically unattractive. Propene or 2-butene or mixtures of propene and 2-butene are used in a mole ratio to 1,4-hexadiene of 0.2/1 to 100/1, preferably in the range of 1/1 to 10/1 and, more preferably, in the range of 2/1 to 4/1. The amount of propene or 2-butene is selected to maximize the composition of 1,4-hexadienes relative to 1,4-pentadienes in the product mixture.

A preferred catalyst system is 10–14 weight percent $Re_2O_7$ on alumina catalyst, which is activated in a flowing air stream at 500° C. for 2–5 hours. The catalyst is then contacted under anhydrous conditions with ethene, propene and cis-1,4-hexadiene at −30° to 200° C. and at a pressure of 140 to 2,000 psig (1,070 to 14,000 kPa). In a still more preferred embodiment, the 10–14 weight percent $Re_2O_7$ on alumina catalyst is placed in a fixed bed and the mixture of mono and diolefin is passed through the bed at a weight hourly space velocity ("WHSV") of 0.5 to 12 g-feed/g-catalyst/hour. The flow rate through the bed is preferably at a WHSV of 0.5 to 5 g-feed/g-catalyst/hour, and most preferably, at a WHSV of 0.5 to 3 g-feed/g-catalyst/hour. When using a fixed bed catalyst, the reactor pressure ranges are as stated above. The reactor temperature is preferably between −10° and 100° C., but more preferably, between 0° and 70° C., and, most preferably, between 0° and 30° C. In an especially preferred embodiment, a 14% $Re_2O_7$ on alumina catalyst is activated in a flowing stream of air at 500° C. for 5 hours in a fixed bed. The reactor is purged and the catalyst is contacted under anhydrous conditions with ethene, propene, and cis-1,4-hexadiene at a temperature between 0° and 30° C. at a pressure of 500 to 800 psig (3,500 to 5,500 kPa), with a WHSV of 0.5 to 3 g-feed/g-catalyst/hour.

In a further embodiment of the invention, the isomerized diolefin is separated from the other metathesis products by any convenient means, such as distillation. Optionally, all other components of the reaction mixture are returned to the metathesis reaction vessel. Optionally, the return stream is mixed with incoming fresh starting olefin feed mixture and the total feed mixture is passed through a fixed bed reactor. For example, 1,4-hexadienes from the metathesis reaction described above are separated from the other products by distillation, gas chromatography, counter current extraction, column chromatography or other separation method and the 1,4-pentadienes, heavy olefins, ethene, propene, and 2-butene are returned to the metathesis reactor. In a more preferred embodiment, the return stream of 1,4-pentadiene, heavy olefins, ethene, propene, and 2-butene is mixed with fresh 1,4-hexadiene, ethene, propene or 2-butene and again passed through a fixed bed of $Re_2O_7$ on alumina catalyst under the conditions recited above. In the preceding illustration, 2-butene may be substituted for propene in the reaction mixture, if desired, or a mixture of propene and 2-butene may be used.

The example below shows the various reaction conditions and feed ratios needed to obtain product with a trans isomer content greater than 60% preferably greater than about 80%. Trans diolefins are kinetically and thermodynamically favored over cis. Cis content greater than 50% is indicative of low per pass conversion conditions.

EXAMPLES

In runs 1–7, 14 wt. % $Re_2O_7$ catalyst supported on alumina, and mixed with quartz, was placed in a 25.4 cm (10 in.)×1.02 cm (0.4 in.) tubular stainless steel reaction vessel, brought to the desired temperature, and contacted with ethene, propene, and 99.9% cis-1,4-hexadiene under the conditions summarized in Table 1a below. The reaction products were determined by gas chromatography and identified as trans/cis-1,4-hexadiene, 1,4-pentadiene, trans/cis-2-butene and heavier alkenes. The conversion of cis-1,4-hexadiene to trans-1,4-hexadiene is observed in each case. In these runs, no positional isomerization was observed.

Table 1b illustrates the conversion of 1,4-pentadiene to trans/cis-1,4-hexadiene in run 8, in the same reaction vessel as runs 1–7. Table 1c presents data for batch operation and shows, in run 10, that trans-1,4-hexadiene as a feed stock yields predominately trans product. Run 9 shows the conversion of cis-1,4-hexadiene to 80/20 trans/cis-1,4-hexadiene under the same reaction conditions. Runs 9 and 10 were performed in a 50 ml stirred reaction vessel.

TABLE

| Table 1a | Run # | | | | | | |
|---|---|---|---|---|---|---|---|
| | 1 | 2 | 3 | 4 | 5 | 6 | 7 |
| 14 wt % $Re_2O_7$ mesh size of support and quartz if used | 20/30 | 20/30 | 20/30 | 30/40 | 40/50 | 30/40 | 20/30 |
| weight ratio of alumina support to quartz g/g | 8.66/ 12.5 | 8.66/ 12.5 | 4.26/ 16.4 | 4.26/ 16.4 | 4.26/ 16.4 | 12.6/ none | 8.5/ none |
| temp. °C. | 30° C. | 30° C. | 30° C. | 30° C. | 30° C. | 0° C. | 100° C. |
| pressure psig (kPa) | 480 (3400) | 620 (4400) | 620 (4400) | 620 (4400) | 620 (4400) | 510 (3600) | 520 (3700) |
| ethene feed rate mole/h | .217 | .217 | .217 | .424 | .424 | .217 | .217 |
| propene feed rate mole/h | .217 | .217 | .217 | .424 | .424 | .217 | .217 |

TABLE-continued

| | | | | | | | |
|---|---|---|---|---|---|---|---|
| 1,4-hexadiene feed rate mole/h | .099 | .099 | .099 | .198 | .198 | .099 | .099 |
| WHSV g-feed/g-cat/h | 2.7 | 2.7 | 5.5 | 10.7 | 10.7 | 1.8 | 2.0 |
| time | 0–10h | 0–21h | 0–2h | 0–1h | 0–1h | 0–1h | 0–1h |
| % recovery 1,4 hexadiene | 27 | 22–26[1] | 33 | 36 | 36 | 34 | 47 |
| trans/cis ratio 1,4 hexadiene | 82/18 | 80.5/19.5 | 81/19 | 70/30 | 79/21 | 76/24 | 25/75 |
| time | 10–20h | | 2–22h | 1–8h | 1–8h | 1–23 h | 1–14h |
| % recovery 1,4 hexadiene | 27 | | 37 | 63 | 46 | 36 | 63 |
| trans/cis ratio 1,4 hexadiene | 77/23 | 82/18 | 54/46 | 66/34 | 45/55 | 32/68 | 4/96 |

| | Run # | | | Run # | |
|---|---|---|---|---|---|
| Table 1b | 8 | Table 1c | | 9 | 10 |
| 14 wt % Re₂O₇ mesh size of support and quartz if used | 30/40 | 14 wt % Re₂O₇ mesh size of support and quartz if used | | 20/30 | 20/30 |
| weight ratio of alumina support to quartz g/g | 12.6/ none | weight ratio of alumina support to quartz g/g | | 5.22/ none | 5.22/ none |
| temp. °C. | 0° C. | temp. °C. | | 12° C. | 12° C. |
| pressure psig | 510 (3600) | pr3essure psig | | 700 (4900) | 700 (4900) |
| ethene feed rate mole/h | .217 | ethene feed rate mole/h | | NA | NA |
| propene feed rate mole/h | .217 | propene feed rate moles | | .025 | .025 |
| 1,4-pentadeien feed rate mole/h | .099 | 1,4-hexadiene feed rate moles | | .061[2] | .061[3] |
| WHSV g-feed/g-cat/h | 1.8 | WHSV g-feed/g-cat/h | | NA | NA |
| time | 22h | time | | 0–4h | 0–4h |
| % recovery 1,4 pentadiene | 26 | % recovery 1,4 hexadiene | | — | — |
| trans/cis ratio 1,4 hexadiene | 86/14 | trans/cis ratio 1,4 hexadiene | | 46/54 | 94/6 |
| time | | time | | 4–19h | 4–24h |
| % recovery 1,4 hexadiene | | % recovery 1,4 hexadiene | | 37 | 27 |
| trans/cis ratio 1,4 hexadiene | | trans/cis ratio 1,4-hexadiene | | 80/20 | 92/8 |

[1]Over the 21 hours the recovery increased from 22% to 26% but the trans/cis ratio remained in the narrow range between 80.5/19.5 to 82/18.
[2]Run 9 feed was 99% cis-1,4 hexadiene.
[3]Rn 10 feed was 98% trans-1,4-hexadiene.

We claim:

1. A method for making trans non-conjugated diolefins of structure

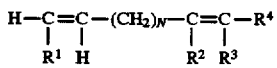

which comprises:

a. selecting isomerizable non-conjugated diolefin with structure

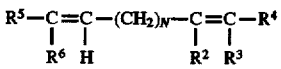

where N is a positive integer from 1 to 5 and $R^2$, $R^3$, $R^4$ and $R^5$, are each hydrogen or an alkyl of 1 to 5 carbons and $R^1$ and $R^6$ are each an alkyl of 1 to 5 carbons and $R^2$, $R^3$, and $R^4$ are the same as in the trans non-conjugated diolefin and when $R^5$ is hydrogen and $R^6$ is an alkyl, the adjacent double bond is greater than 50% cis;

b. selecting a first olefin from the group consisting of:

where N is a positive integer from 1 to 5 and $R^2$, $R^3$, and $R^4$ are each hydrogen or an alkyl of 1 to 5 carbons and $R^1$ is an alkyl of 1 to 5 carbons (1) olefins having the structure

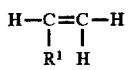

(2) olefins having the structure:

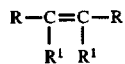

and (3) mixtures of olefin 1 and olefin 2 where $R^1$ is the same as $R^1$ of the trans non-conjugated diolefin;

c. selecting a second olefin which is different than the first olefin from the group consisting of (1) an olefin having the structure:

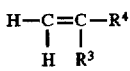

(2) an olefin having the structure:

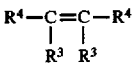

and (3) mixtures of olefin 1 and olefin 2 where $R^3$ and $R^4$ are the same as $R^3$ and $R^4$ of the diolefin selected in step a;

d. mixing the selected diolefin with the selected first olefin and the selected second olefin in a mole ratio of first olefin to diolefin within the range of about 0.2/1 to 100/1 and a mole ratio of the selected second olefin to diolefin within the range of about 0.2/1 to 100/1 to form an olefin reaction mixture; and e. contacting the olefin reaction mixture in a reaction vessel at a temperature in the range of –30° to 200° C. at a pressure in the range of 140 to 2,000 psig (1,070 to 14,000 kPa) with a non-acidic metathesis catalyst selected from the group consisting of homogeneous metal catalysts and heterogeneous metal catalysts wherein the metal is selected from the group consisting of W, Mo, Co, Ta, Nb, Cr, and Re to form the selected trans nonconjugated diolefin isomer product.

2. The method of claim 1, in which the trans nonconjugated diolefin isomer product is separated from the reaction mixture after passing through the reaction vessel and at least a portion of the other olefin and diolefin components of the reaction mixture are returned to the reaction vessel.

3. The method of claim 1, in which the catalyst is promoted by a promoter selected from the group consisting of a tetraalkyl tin compound of 1 to 5 carbons in each alkyl or a trialkyl aluminum compound of 1 to 5 carbons in each alkyl.

4. The method of claim 1, in which the temperature is in the range of –10° C. and 100° C., the pressure is between 400 and 1500 psig (1,070 and 10,400), and the ratio of first olefin to diolefin is in the range of 1/1 to 10/1, and the ratio of second olefin to diolefin is in the range of 1/1 to 10/1.

5. The method of claim 1, in which the catalyst is a heterogeneous catalyst selected from the group consisting of $Re_2O_7$, CoO, $MoO_3$, $WO_3$ and mixtures thereof, each in the range of 5 to 30 weight percent of the total catalyst weight and supported on a support selected from the group consisting of alumina and silica in a fixed bed and contacted with the olefin mixture at a WHSV of 0.5 to 12 g-feed/g-catalyst/hour in a continuous reaction.

6. The method of claim 2, in which the temperature is in the range of –10° C. and 100° C., the pressure is between 400 and 1500 psig (2,900 and 10,400 kPa), the ratio of first olefin to diolefin is in the range of 1/1 to 10/1, and the ratio of second olefin to diolefin is in the range of 1/1 to 10/1.

7. The method of claim 3, in which the temperature is in the range of –10° C. and 100° C., the reactor pressure is between 400 and 1500 psig (2,900 and 10,400 kPa), the ratio of first olefin to diolefin is in the range of 1/1 to 10/1, and the ratio of second olefin to diolefin is in the range of 1/1 to 10/1.

8. The method of claim 5, in which the temperature is in the range of –10° C. and 100° C., the pressure is between 400 and 1500 psig (2,900 and 10,400 kPa), and a WHSV of 0.5 to 5 g-feed/g-catalyst/hour, the ratio of first olefin to diolefin is in the range of 1/1 to 10/1, and the ratio of second olefin to diolefin is in the range of 1/1 to 10/1.

9. The method of claim 4, in which the temperature is in the range of 0° C. and 30° C., the pressure is between 500 and 800 psig (3,500 and 5,500 kPa), the ratio of first olefin to diolefin is in the range of 2/1 to 4/1, the ratio of second olefin to diolefin is in the range of 2/1 to 4/1.

10. The method of claim 6, in which the temperature is in the range of 0° C. and 30° C., the pressure is between 500 and 800 psig (3,500 and 5,500 kPa), the ratio of first olefin to diolefin is in the range of 2/1 to 4/1, the ratio of second olefin to diolefin is in the range of 2/1 to 4/1.

11. The method of claim 7, in which the temperature is in the range of 0° C. and 30° C., the pressure is between 500 and 800 psig (3,500 and 5,500 kPa), the ratio of first olefin to diolefin is in the range of 2/1 to 4/1, the ratio of second olefin to diolefin is in the range of 2/1 to 4/1.

12. The method of claim 8, in which the temperature is in the range of 0° C. and 30° C., the pressure is between 500 and 800 psig (3,500 and 5,500 kPa), and a WHSV of 0.5 to 3 g-feed/g-catalyst/hour, the ratio of first olefin to diolefin is in the range of 2/1 to 4/1, the ratio of second olefin to diolefin is in the range of 2/1 to 4/1.

13. A method according to claim 1, in which the catalyst is a homogeneous catalyst selected from the group consisting of $Mo(NO)_2Cl_2$ $(PPh_3)_2$/ETAlCl$_2$, $Mo(CO)_4$ (Pyridine)$_2$/Bu$_4$NCl/Me$_3$Al$_2$Cl$_3$ or carbene complexes of Ta, Nb, or Cr.

14. A method of preparing trans-1,4-hexadiene consisting essentially of contacting an olefin reaction feed mixture comprising cis-1,4-hexadiene, ethane and an olefin selected from the group consisting of propane, 2-butane, and mixtures of propene and 2-butene, under effective conditions with a metathesis catalyst which comprises one or more compounds selected from the group consisting of rhenium oxide ($Re_2O_7$), tungsten oxide ($WO_3$), cobalt oxide (CoO), or molybdenum oxide ($MoO_3$); the selected catalyst compound being loaded onto a solid support at a loading of between 5 and 30 wt % in a fixed catalyst bed.

15. A method in accordance with claim 14, wherein contacting the feed mixture with the metathesis catalyst occurs at a temperature in the range of –30° to 200° C. and a pressure in the range of 140 to 2000 psig (1,070 to 14,000 kPa) and a WHSV of 0.5 to 12 g-feed/g-catalyst/hour; the olefin reaction mixture mole ratio of propene to 1,4-hexadiene is greater than 1/1, the olefin reaction mixture mole ratio of ethene to 1,4-hexadiene is greater than 0.5 to 1 and the olefin reaction mixture mole ratio of propene to ethene is at least 2/1.

16. A method in accordance with claim 14, wherein contacting the feed mixture with the metathesis catalyst occurs at a temperature in the range of −10° to 100° C. and a pressure in the range of 400 to 1500 psig (2,900 to 10,400 kPa) and a WHSV of 0.5 to 5 g-feed/g-catalyst/hour; the catalyst loading on the solid support is in the range of 10 to 14 weight percent; the olefin reaction mixture mole ratio of propene to 1,4-hexadiene is in the range of 1/1 to 10/1, the olefin reaction mixture mole ratio of ethene to 1,4-hexadiene is in the range of 1/1 to 10/1 and the olefin reaction mixture mole ratio of propene to ethene is at least 2/1.

17. A method in accordance with claim 14, wherein contacting the feed mixture with the metathesis catalyst occurs at a temperature in the range of 0° to 30° C. and a pressure in the range of 500 to 800 psig 3,500 to 5,500 kPa) and a WHSV of 0.5 to 3 g-feed/g-catalyst/hour; the olefin reaction mixture mole ratio of propene to 1,4-hexadiene is in the range of 2/1 to 4/1, the olefin reaction mixture mole ratio of ethene to 1,4-hexadiene is in the range of 2/1 to 4/1 and the olefin reaction mixture mole ratio of propene to ethene is at least 2/1.

18. A method according to claim 14, in which the trans-1,4-hexadiene product is separate and at least a portion of the other olefin and diolefin components of the product mixture are returned to the olefin reaction mixture.

19. A method according to claim 14, in which the catalyst is promoted by a promoter selected from the group consisting of a tetraalkyl tin compound of 1 to 5 carbons in each alkyl or a trialkyl aluminum compound of 1 to 5 carbons in each alkyl.

20. A method according to claim 19, wherein the promoter is tetramethyl tin.

* * * * *